(12) United States Patent
Fiedler et al.

(10) Patent No.: US 7,278,786 B2
(45) Date of Patent: Oct. 9, 2007

(54) METHOD AND APPARATUS FOR TRIGGERING IMAGE ACQUISITION IN A C-ARM SYSTEM BY A ROTARY ENCODER

(75) Inventors: Klaus Fiedler, Aachen (DE); Jens Wiegert, Aachen (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 40 days.

(21) Appl. No.: 10/555,575

(22) PCT Filed: Apr. 26, 2004

(86) PCT No.: PCT/IB2004/001375

§ 371 (c)(1),
(2), (4) Date: Nov. 4, 2005

(87) PCT Pub. No.: WO2004/098411

PCT Pub. Date: Nov. 18, 2004

(65) Prior Publication Data

US 2007/0015986 A1    Jan. 18, 2007

(30) Foreign Application Priority Data

May 6, 2003   (EP) ................................. 03101250

(51) Int. Cl.
*A61B 6/08* (2006.01)
(52) U.S. Cl. ......................................... 378/205; 378/4
(58) Field of Classification Search ............. 378/4–20, 378/205, 62, 114, 115, 197; 250/231.13
See application file for complete search history.

(56) References Cited

U.S. PATENT DOCUMENTS

| | | | |
|---|---|---|---|
| 4,157,472 A | 6/1979 | Beck et al. .................. 250/445 |
| 5,175,754 A * | 12/1992 | Casey et al. .................... 378/4 |
| 5,432,339 A * | 7/1995 | Gordon et al. ......... 250/231.13 |
| 5,932,874 A * | 8/1999 | Legg et al. ............ 250/231.13 |
| 6,079,876 A | 6/2000 | Schuetz ....................... 378/205 |
| 6,233,308 B1 | 5/2001 | Hsieh .......................... 378/62 |
| 7,123,680 B2 * | 10/2006 | Katada et al. ................ 378/16 |
| 2002/0085681 A1 | 7/2002 | Jensen ....................... 378/197 |
| 2002/0090058 A1 | 7/2002 | Yasuda et al. .............. 378/205 |

FOREIGN PATENT DOCUMENTS

| | | |
|---|---|---|
| EP | 0 325 656 | 8/1989 |
| GB | 1 569 885 | 6/1980 |

* cited by examiner

*Primary Examiner*—Jurie Yun

(57) ABSTRACT

Method of generating an image of an object by means of an imaging system which has a radiation source that rotates relative to the object about an axis of rotation within a defined rotation angle range, said radiation source projecting radiation onto a radiation detector in order to record projection data, wherein at predefinable relative rotation angle positions of the radiation source a signal projection data is generated, and also apparatus for carrying out this method.

8 Claims, 1 Drawing Sheet

Figure 1:
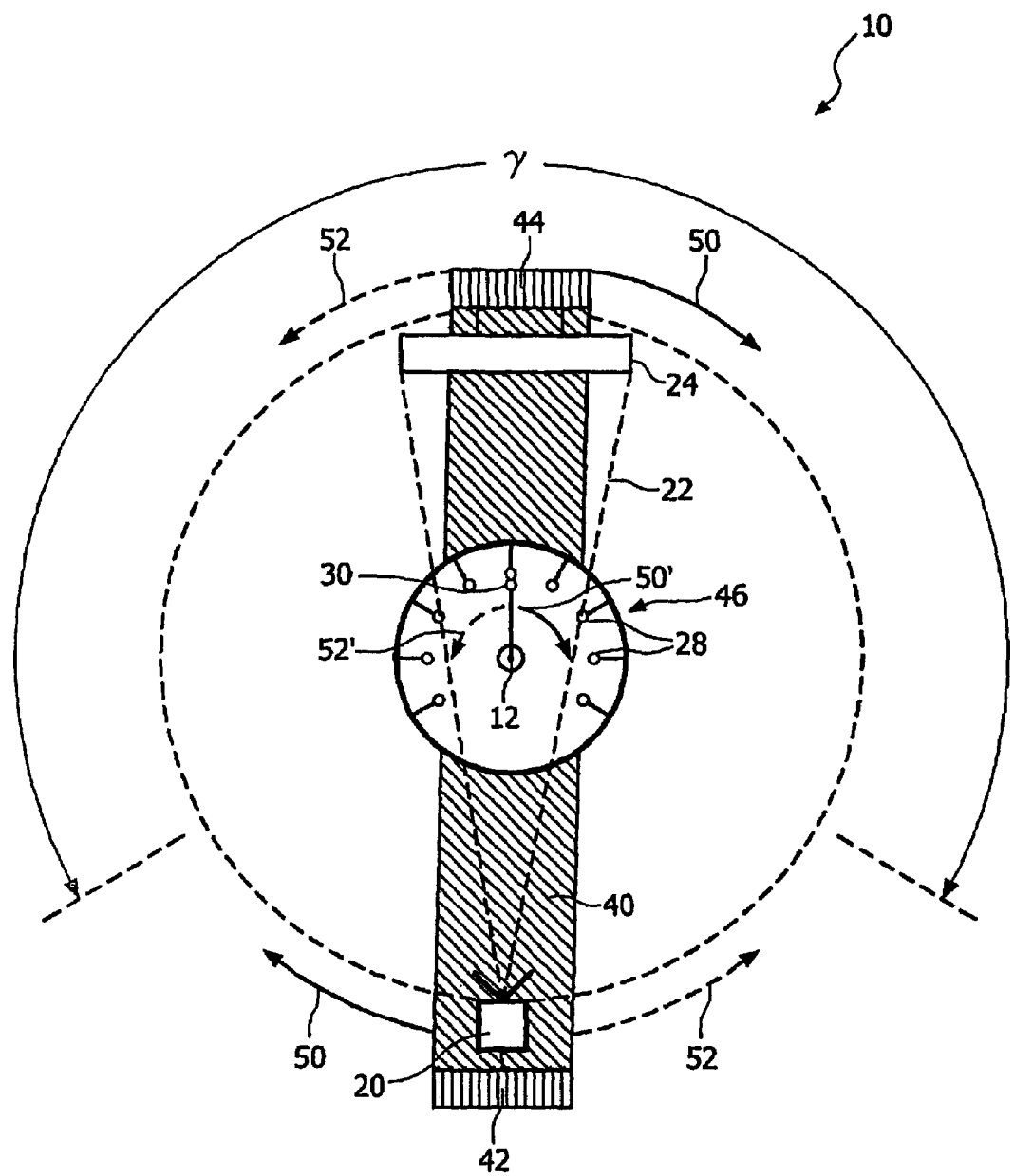

METHOD AND APPARATUS FOR TRIGGERING IMAGE ACQUISITION IN A C-ARM SYSTEM BY A ROTARY ENCODER

The invention relates to a method of generating an image of an object by means of an imaging system which has a radiation source that rotates relative to the object about an axis of rotation within a defined rotation angle range, said radiation source projecting radiation onto a radiation detector in order to record projection data, and also to an apparatus suitable for carrying out this method.

By contrast to a computer tomography system which has a gantry that can rotate about an axis of rotation at any desired rotation angle, in C-arc systems there is the restriction that the maximum rotation angle range that can be passed through is limited and is for example 240°, with the C-arc being connected by way of a cable connection. As a result of these conditions, when passing through the maximum angle range, there is necessarily an acceleration and braking phase with the result that there are, at a constant recording frequency, different angular spacings between successive projection data recording processes. This means that deviations from expected or calculated angular spacings or angular positions of successive projection images on account of mechanical, electrical or other influences cannot be reconstructed and hence cannot undergo subsequent correction. The same problem arises in the case of unintentional fluctuations in the recording frequency.

It is an object of the invention to eliminate the above-mentioned sources of error and to provide a method and an apparatus for imaging in which the projection images can be recorded without being affected by deviations from a predefined recording frequency or rotation speed.

With regard to the method, this object is achieved according to the invention by a method of generating an image of an object by means of an imaging system which has a radiation source that rotates relative to the object about an axis of rotation within a limited rotation angle range, said radiation source projecting radiation onto a radiation detector in order to record projection data, wherein at predefinable relative rotation angle positions of the radiation source a signal which is used to trigger recording of the projection data is generated.

In the invention, therefore, the angular positions of the projection images are not derived from two physical variables (rotation speed and recording frequency) but rather are triggered directly at predefinable rotation angle positions of the radiation source, so that there is no undesirable error in the angular spacing of the projection images even in the event of changes or unintentional fluctuations in the rotation speed of the radiation source or in the recording frequency. As a result, the occurrence of specific artefacts in the reconstructed volume image is avoided. Moreover, the calibration of the system is less complicated, since the rotation angle belonging to a projection image can be easily assigned to the latter. Furthermore, the requirements in terms of mechanical reproducibility (constancy of the angular speed) of the rotation movement are not very high, that is to say certain fluctuations can be permitted.

Although in principle it could be possible to vary the rotation angle positions during an imaging cycle, e.g. they could be continually adapted to certain parameters, it is provided that the rotation angle positions are fixedly predefined, and specifically with the same mutual angular spacings, so that in a complete pass of the radiation source through a specific rotation angle range relative to the object that is to be examined a desired number of images can be recorded with the same angular spacing.

The signal generated to trigger recording of the projection data can be generated in any technically expedient and possible manner, in particular mechanically, electrically, optically and/or electromagnetically.

With regard to the apparatus, the object of the invention is achieved by an apparatus for generating an image of an object, which has a radiation source that rotates relative to the object about an axis of rotation within a defined rotation angle range, said radiation source projecting radiation onto a radiation detector in order to record projection data, wherein the rotating radiation source is coupled to angle sensors which at predefinable relative rotation angle positions of the radiation source generate a signal for triggering recording of the projection data.

The radiation source may be an X-ray radiation source for cone beam imaging which is arranged on a C-arm, wherein the angle sensors are integrated in a pivot bearing of the C-arm. Advantageous developments of the apparatus are indicated in the further dependent claims.

The invention will be further described with reference to an example of embodiment shown in the drawing to which, however, the invention is not restricted.

FIG. 1 shows a schematic axial view of a C-arm volume imaging system known per se, which according to the invention is provided with angle sensors.

FIG. 1 shows a schematic view of one embodiment of the invention in the form of a C-arc system for volume imaging, comprising a C-arm 40 that rotates about an axis of rotation 12. The C-arm 40, the legs 42, 44 of which extend perpendicular to the plane of the drawing and parallel to the axis of rotation 12, bears an X-ray radiation source 20 and a detector surface 24 and can be moved over a rotation angle range of in each case about 240°. In the region of a pivot bearing 46 of the C-arm 40, which allows rotation of the C-arm by means of a rotary drive (not shown) about the axis of rotation 12 either in the clockwise direction (arrow 50) or in the counterclockwise direction (arrow 52), there are arranged fixed angle sensors 28 and a rotating angle sensor 30 (which rotates with said C-arm as shown by the arrows 50' 52').

A central control unit (not shown) controls the X-ray radiation source 20, the recording of data at the detector surface 24 and a rotary drive of the C-arm 40 (rotation speed and position). According to the invention, the control unit also receives rotation-angle-position-related signals from the fixed angle sensors 28 and the angle sensor 30 arranged on the C-arm 40, wherein a signal is always generated when the angle sensor 30 passes one of the fixed angle sensors 28. The angle sensors 28 and 30 are shown only schematically in FIG. 1 and may generate a signal mechanically, electrically, optically and/or electromagnetically. By way of example, electromechanical contacts may be provided, by means of which an electrical signal is generated. Alternatively, optical sensors in the manner of a light barrier may be used. Magnetic or electromagnetic signal generators, such as Hall sensors for example, are likewise conceivable.

The fixed angle sensors 28 are arranged at the same mutual angular spacings within the rotation angle range covered by the C-arm.

Although a larger number of fixed angle sensors and a single angle sensor which moves along with the C-arm are provided in FIG. 1, the arrangement could also of course be reversed, i.e. there could be provided one fixed angle sensor and a number of angle sensors which move. Although the fixed angle sensors preferably have a constant mutual angular spacing, an arrangement which differs therefrom or which may possibly even be variable could also be selected. Finally, there could be provided a relatively large number of angle sensors, wherein in that case, during an imaging cycle, possibly not every individual angle sensor would generate a signal or possibly its signal would not actually be used to trigger a recording, but rather only individual signals, for example every nth signal, would be used, so that the effective number of angle sensors is reduced or the effective mutual angular spacing is increased if this is desired in any specific case. In this way, during a complete pass of the C-arm, images or projection data at different spacings can be recorded, the mutual angular spacing of which is narrower in particularly interesting regions in which for example the signals of each individual successive angle sensor are used to trigger a projection data recording, whereas in less interesting regions a larger image spacing is sufficient and a larger mutual angular spacing is produced (in this case, for example, only every second, third or suchlike signal from successive angle sensors is used to trigger recording). The technical implementation of such a use of all or only some selected signals may be effected mechanically or electrically by switching off individual angle sensors or whole groups of angle sensors or else by means of computers and software by selecting desired signals.

By virtue of the invention, the abovementioned disadvantages are avoided. A further advantage of the invention is that a dedicated calibration which has heretofore been required for each recording mode (rotation speed, recording frequency), which was necessary since on account of timer and mechanical inaccuracies in each case new absolute angles are produced which do not coincide with those of the other sequences, can now be omitted since the absolute angular positions no longer change at different rotation speeds. The rotation speed may subsequently be varied at will without adjusting the recording frequency.

LIST OF REFERENCES

10 imaging system
12 axis of rotation (longitudinal axis)
20 X-ray radiation source
22 X-ray bundle
24 detector surface
26 control unit
28 fixed angle sensor
30 angle sensor
40 C-arm
42, 44 leg
46 pivot bearing
50, 52 arrow
50', 52' arrow

The invention claimed is:

1. An imaging apparatus comprising:
   a c-arm that rotates within a limited rotation angle range about an object to be imaged;
   a radiation source coupled to said c-arm, said radiation source projecting radiation onto a radiation detector in order to record projection data; and
   a plurality of rotation angle sensors, comprising one or more fixed angle sensors and one or more moving angle sensors, wherein a signal for recording of the projection data is generated when select rotation angle sensors align.

2. The apparatus as claimed in claim 1, wherein the rotation angle sensors are mechanical, electrical, optical and/or electromechanical angle sensors.

3. The apparatus as claimed in claim 1, wherein the fixed angle sensors or the moving angular sensors are positioned with the same angular spacings.

4. The apparatus of claim 1, wherein the select rotation angle sensors align at predefined intervals.

5. The apparatus of claim 1, wherein the select rotation angle sensors align at predetermined fixed positions.

6. A method for imaging an object with an x-ray imaging apparatus that rotates within a limited angle range about the object to be imaged comprising:
   providing a radiation source coupled to the x-ray imaging apparatus;
   projecting radiation onto a radiation detector in order to record projection data;
   providing a plurality of rotation angle sensors, comprising one or more fixed angle sensors and one or more moving angle sensors; and
   recording the projection data when select rotation angle sensors align.

7. The method of claim 6, wherein the rotation angle sensors are mechanical, electrical, optical and/or electromechanical angle sensors.

8. The method of claim 6, wherein the select rotation angle sensors align at predetermined fixed positions.

* * * * *